United States Patent [19]
Yankee

[11] 3,978,112
[45] Aug. 31, 1976

[54] 8β,11β,12α-17-PHENYL-PGF$_{2β}$ COMPOUNDS

[75] Inventor: Ernest W. Yankee, Portage, Mich.

[73] Assignee: The Upjohn Company, Kalamazoo, Mich.

[22] Filed: Oct. 29, 1974

[21] Appl. No.: 518,431

Related U.S. Application Data

[60] Division of Ser. No. 374,405, June 28, 1973, which is a continuation-in-part of Ser. No. 289,317, Sept. 15, 1972, abandoned.

[52] U.S. Cl. .......................... 260/473 A; 260/520 B
[51] Int. Cl.$^2$ .................... C07C 65/22; C07C 65/14
[58] Field of Search ............ 260/473 A, 520, 520 B

[56] References Cited
UNITED STATES PATENTS 3,862,984  1/1975  Pike et al. ...................... 260/514 D

FOREIGN PATENTS OR APPLICATIONS 2,154,309  5/1972  Germany

OTHER PUBLICATIONS

Corey et al., J. Org. Chem. 37, 3043 (1972).
Gandolfi et al., Tet. Letters, 4303 (1972).

*Primary Examiner*—Paul J. Killos
*Attorney, Agent, or Firm*—Morris L. Nielsen; Robert A. Armitage

[57] ABSTRACT

This invention is a group of 8-β, 12-α-PG$_2$ (prostaglandin-type) analogs having variable chain length, or methyl or phenyl substitution in the hydroxy-substituted side-chain, and processes for making them. These compounds are useful for a variety of pharmacological purposes, including anti-ulcer, inhibition of platelet aggregation, increase of nasal patency, and labor inducement at term.

6 Claims, No Drawings

8β,11β,12α-17-PHENYL-PGF$_{2β}$ COMPOUNDS

CROSS REFERENCE TO RELATED APPLICATIONS

This is a division of application Ser. No. 374,405, filed June 28, 1973, which is a continuation-in-part of my copending application Ser. No. 289,317 filed Sept. 15, 1972, now abandoned.

The present invention relates to prostaglandin analogs, for which the essential material constituting a disclosure thereof is incorporated by reference here from Ser. No. 518,436, filed Oct. 29, 1974, now U.S. Pat. No. 3,969,396.

I claim:

1. An optically active compound of the formula

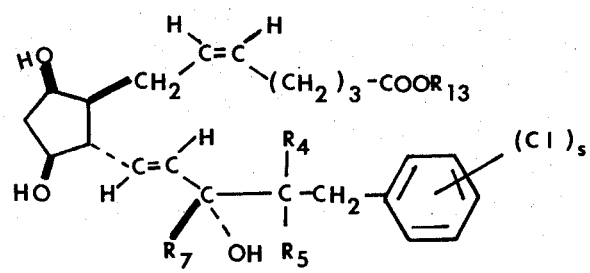

wherein $R_4$, $R_5$, and $R_7$ are hydrogen or methyl, being the same or different;
wherein $R_{13}$ is hydrogen, alkyl of 1 to 12 carbon atoms, inclusive, cycloalkyl of 3 to 10 carbon atoms, inclusive, aralkyl of 7 to 12 carbon atoms, inclusive, phenyl, or phenyl substituted with 1, 2, or 3 chloro or alkyl of 1 to 4 carbon atoms, inclusive; and
wherein $s$ is zero, 1, 2, or 3;
including the lower alkanoates thereof, and the pharmacologically acceptable salts thereof when $R_{13}$ is hydrogen.

2. 17-(p-chlorophenyl)-18,19,20-trinor-8β,11β,12α-PGF$_{2β}$, a compound according to claim 1.

3. 17-(p-chlorophenyl)-18,19,20-trinor-8β,11β,12α-PGF$_{2β}$, methyl ester, a compound according to claim 1.

4. 17-Phenyl-18,19,20-trinor-8β,11β,12α-PGF$_{2β}$, a compound according to claim 1.

5. 17-Phenyl-18,19,20-trinor-8β,11β,12α-PGF$_{2β}$, methyl ester, a compound according to claim 1.

6. An optically active compound of the formula

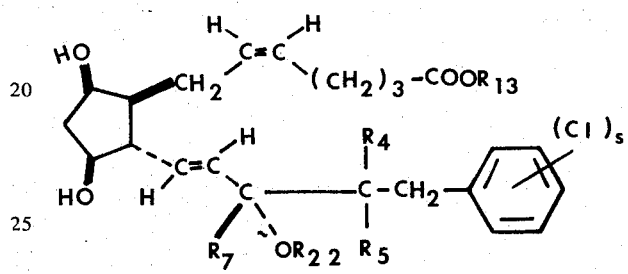

wherein $R_4$, $R_5$, and $R_7$ are hydrogen or methyl, being the same or different;
wherein $R_{13}$ is hydrogen, alkyl of 1 to 12 carbon atoms, inclusive, cycloalkyl of 3 to 10 carbon atoms, inclusive, aralkyl of 7 to 12 carbon atoms, inclusive, phenyl, or phenyl substituted with 1, 2, or 3 chloro or alkyl of 1 to 4 carbon atoms, inclusive; and
wherein $R_{22}$ is alkyl of 1 to 4 carbon atoms, inclusive;
wherein $s$ is zero, 1, 2, or 3;
including the lower alkanoates thereof, and the pharmacologically acceptable salts thereof when $R_{13}$ is hydrogen.

* * * * *